(12) United States Patent
Cerofolini (10) Patent No.: US 7,691,064 B2
(45) Date of Patent: Apr. 6, 2010

(54) ULTRASOUND IMAGING METHOD COMBINED WITH THE PRESENCE OF CONTRAST MEDIA IN THE BODY UNDER EXAMINATION

(75) Inventor: Marino Cerofolini, Subbiano (IT)

(73) Assignee: Esaote, S.p.A., Milan (IT)

( * ) Notice: Subject to any disclaimer, the term of this patent is extended or adjusted under 35 U.S.C. 154(b) by 727 days.

(21) Appl. No.: 10/935,978

(22) Filed: Sep. 8, 2004

(65) Prior Publication Data

US 2005/0054928 A1 Mar. 10, 2005

(30) Foreign Application Priority Data

Sep. 9, 2003 (EP) .................................. 03425581

(51) Int. Cl.
*A61B 8/00* (2006.01)
*A61B 8/14* (2006.01)

(52) U.S. Cl. .................... 600/458; 600/443; 600/454

(58) Field of Classification Search ................ 600/455, 600/454, 441, 443, 437, 456, 458; 128/916
See application file for complete search history.

(56) References Cited

U.S. PATENT DOCUMENTS

| | | | | |
|---|---|---|---|---|
| 5,678,553 A * | 10/1997 | Uhlendorf et al. | ........... | 600/458 |
| 5,812,678 A * | 9/1998 | Scalise et al. | .................. | 381/67 |
| 5,833,614 A * | 11/1998 | Dodd et al. | .................. | 600/447 |
| 5,856,955 A * | 1/1999 | Cole et al. | ................... | 367/138 |
| 5,913,823 A * | 6/1999 | Hedberg et al. | ............. | 600/443 |
| 5,919,138 A * | 7/1999 | Ustuner | ....................... | 600/443 |
| 5,961,463 A | 10/1999 | Rhyne et al. | ................. | 600/458 |
| 5,980,459 A | 11/1999 | Chiao et al. | .................. | 600/447 |
| 6,005,827 A * | 12/1999 | Hossack et al. | ................ | 367/7 |
| 6,045,505 A * | 4/2000 | Holley et al. | ................. | 600/441 |
| 6,050,947 A | 4/2000 | Rhyne et al. | ................. | 600/447 |
| 6,066,098 A | 5/2000 | Masotti et al. | .............. | 600/443 |
| 6,074,348 A * | 6/2000 | Chiao et al. | .................. | 600/443 |
| 6,108,572 A * | 8/2000 | Panda et al. | .................. | 600/407 |
| 6,117,082 A | 9/2000 | Bradley et al. | .............. | 600/447 |
| 6,132,377 A * | 10/2000 | Bolorforosh et al. | ........ | 600/458 |
| 6,146,330 A * | 11/2000 | Tujino et al. | ................. | 600/443 |
| 6,171,245 B1 * | 1/2001 | Wilkening et al. | .......... | 600/458 |
| 6,186,949 B1 * | 2/2001 | Hatfield et al. | .............. | 600/443 |
| 6,213,947 B1 * | 4/2001 | Phillips | ...................... | 600/443 |
| 6,221,018 B1 * | 4/2001 | Ramamurthy et al. | ....... | 600/443 |

(Continued)

OTHER PUBLICATIONS

Chomas, James E. et al. Subharmonic Phase-Inversion for Tumor Perfusion Estimation. IEEE Ultrasonic Symposium. 2001. pp. 1713-1716.*

(Continued)

*Primary Examiner*—Eric F Winakur
*Assistant Examiner*—Helene Bor
(74) *Attorney, Agent, or Firm*—Woodard, Emhardt, Moriarty, McNett & Henry LLP (57) ABSTRACT

An ultrasound imaging method for use in the presence of contrast agents is disclosed in which acoustic waves are transmitted at a first fundamental transmission frequency and are focused on at least one scan line. Acoustic beams reflected from the body under examination and the contrast agents are separated into at least one harmonic or subharmonic components along with the fundamental frequency component. The amplitudes of these components compared to determine whether the reflecting material is either body tissue or the contrast agent.

21 Claims, 6 Drawing Sheets

U.S. PATENT DOCUMENTS

| | | | |
|---|---|---|---|
| 6,226,352 B1 * | 5/2001 | Salb | 378/98.9 |
| 6,290,647 B1 * | 9/2001 | Krishnan | 600/441 |
| 6,309,356 B1 * | 10/2001 | Ustuner et al. | 600/443 |
| 6,425,869 B1 * | 7/2002 | Rafter et al. | 600/458 |
| 6,494,839 B1 | 12/2002 | Averkiou | 600/443 |
| 6,514,211 B1 * | 2/2003 | Baura | 600/490 |
| 6,544,184 B1 * | 4/2003 | Guracar | 600/458 |
| 6,589,179 B2 * | 7/2003 | Criton et al. | 600/454 |
| RE38,209 E * | 8/2003 | Yamazaki et al. | 600/455 |
| 6,626,836 B2 * | 9/2003 | Mao et al. | 600/455 |
| 6,752,762 B1 * | 6/2004 | DeJong et al. | 600/458 |
| 6,783,496 B2 * | 8/2004 | Hao et al. | 600/458 |
| 6,796,944 B2 * | 9/2004 | Hall | 600/458 |
| 6,890,301 B2 * | 5/2005 | Jago et al. | 600/437 |
| 6,899,681 B1 * | 5/2005 | Phillips et al. | 600/458 |
| 6,918,876 B1 * | 7/2005 | Kamiyama | 600/447 |
| 6,926,671 B2 * | 8/2005 | Azuma et al. | 600/459 |
| 6,953,434 B2 * | 10/2005 | Hao et al. | 600/458 |
| 6,960,169 B2 * | 11/2005 | Mao et al. | 600/458 |
| 6,967,975 B2 * | 11/2005 | Van Stalen et al. | 370/535 |
| 6,971,991 B2 * | 12/2005 | Lasser et al. | 600/437 |
| 7,011,632 B2 * | 3/2006 | Steinbacher et al. | 600/437 |
| 7,025,724 B2 * | 4/2006 | Adam et al. | 600/437 |
| 7,044,914 B2 * | 5/2006 | Kawagishi et al. | 600/458 |
| 7,066,886 B2 * | 6/2006 | Song et al. | 600/443 |
| 2001/0051771 A1 * | 12/2001 | Bradley et al. | 600/443 |
| 2002/0002333 A1 * | 1/2002 | Angelsen et al. | 600/443 |
| 2002/0138003 A1 * | 9/2002 | Bukshpan | 600/458 |
| 2004/0059225 A1 * | 3/2004 | Hao et al. | 600/458 |
| 2005/0148877 A1 * | 7/2005 | Guo et al. | 600/459 |
| 2006/0173342 A1 * | 8/2006 | Panda et al. | 600/459 |

OTHER PUBLICATIONS

"Spaceborn Radar Remote Sensing: Applications and Techniques", Charles Elachi, Institute of Electrical and Electronics Engineers Press, New York, Dec. 1988.

"Coded Excitation System for Improving the Penetration of Real-Time Phased Array Imaging Systems", Matthew O'Donnel, IEEE Transaction on Ultrasonics, Ferroelectrics and Frequency Control, vol. 39, No. 3 May 1992.

* cited by examiner

ULTRASOUND IMAGING METHOD COMBINED WITH THE PRESENCE OF CONTRAST MEDIA IN THE BODY UNDER EXAMINATION

CROSS-REFERENCE TO RELATED APPLICATION

The present application claims the benefit of European Patent Application Serial No. EP03425581.0 filed on Sep. 9, 2003, which is hereby incorporated by reference in its entirety.

BACKGROUND OF THE INVENTION

In diagnostic ultrasonic imaging, several modes are known for processing electroacoustic return signals. These different modes have the purpose of displaying different types of tissues or objects that may be more or less echogenic.

Static tissues typically have a good echogenicity and are optimally detectable by ultrasonic imaging at the fundamental frequency by using B-mode imaging. In this mode, as is well known, the envelope of the return signal is detected, and the envelope amplitude is correlated to a grey scale, thereby forming an image. B-mode images at the fundamental transmission frequency are high-quality images, as the transmitted signal may consist of a broadband pulse, i.e. a very short pulse, which ensures an optimized resolution.

Static tissues, and particularly soft tissues, also generate nonlinear reflected signals. The generated return signal not only contains a fundamental component, i.e. at the same frequency as the transmitted beam, but also comprises nonlinear components, as components at the second or higher-order harmonics of the fundamental transmission frequency.

Highly perfused tissues or blood flows or other body flows are poorly echogenic, i.e. generate reflection contributions well below the intensity of the reflection contributions generated by static tissues. This limitation was accordingly obviated by using substances that amplify the reflection response and are introduced in the blood flows. These substances, known as contrast agents, have a strongly nonlinear reflection response, and therefore generate return signal contributions at the second harmonic of the transmitted beam fundamental frequency. The harmonic imaging mode, developed for contrast agent ultrasonic imaging, removes the fundamental frequency contributions of the return signal and used the second harmonic components generated by contrast agents for image reconstruction.

Nevertheless, as mentioned above with respect to soft tissues, these tissues also generate nonlinear contributions to the return signals, such that it is difficult or impossible to differentiate between return signals in blood flow from soft tissue and return signals due to the presence of contrast agents.

U.S. Pat. No. 6,066,098 teaches an ultrasonic imaging method which does not only use a certain frequency of the return signal, but acquires the whole spectrum of the received signal frequencies. As this spectrum is characteristic for each type of tissue, this method permits the identification of the type of tissue that generated the reflected signal at a predetermined scanning depth and to differentiate tissue contributions from contrast agent contributions in the return signal.

From documents U.S. Pat. No. 6,290,647 and U.S. Pat. No. 6,117,082, it is known to use another characteristic of contrast agents to differentiate the contrast agents from tissue in ultrasonic imaging. In deed, when the transmitted signal is exposed to an appropriate mechanical pressure, contrast agent return signals may be excited, thereby creating signal components at a subharmonic of the transmitted signal frequency. Such subharmonic frequency is not substantially present in the reflected signals generated by physiological tissues. The two documents show that ultrasonic imaging of regions that carry contrast agents may be performed by using components of the subharmonic signal, alternatively or in addition to the harmonic component of the return signal.

Nevertheless, the excitation of the subharmonic components of the return signal generated by contrast agents requires the transmitted pulses to be relatively long, and such time length of transmitted pulses causes an image quality degradation in terms of resolution, as well as the presence of side lobes and generation of artifacts. On the other hand, traditional B-mode images, obtained by using the linear component of the return signal permits, as mentioned above, the generation of high quality images.

It shall be further noted that the use of contrast agent signals is not generally designed for B-mode imaging, but for imaging in a narrow sense, and especially for detecting the presence of contrast agents and possibly the perfusion characteristics thereof, or for determining the speed or amount of flow.

Due to the above, the methods taught by U.S. Pat. Nos. 6,290,647 and 6,117,082 involve a number of image quality restrictions. Problems also arise in the excitation and reception of subharmonic signals, as the band widths of ultrasonic probes are generally insufficient to ensure the reception of harmonic and subharmonic frequencies of the fundamental transmission frequency.

SUMMARY OF THE INVENTION

The present invention has the object of providing a method that accurately distinguishes contrast agents from body tissue, and providing an imaging mode that combines B-mode image quality of the linear components of the received signal with the information that is expected to be acquired by using contrast agents.

A further object of the present invention is to allow the inventive method to be used with continuously moving organs, such as the heart.

The present invention achieves the above purposes by providing an imaging method in which the fundamental component, the harmonic components and the subharmonic components are separated in the return signal. The amplitudes for each of the fundamental, harmonic or subharmonic frequency components at each reflected point along a scan line are stored. The nature of each reflected point is determined by the amplitudes of the fundamental, harmonic and subharmonic components of the return signal in a manner such that a reflected point is determined to be a contrast agent when the subharmonic component of the return signal has an amplitude above a predetermined minimum amplitude.

According to an improvement, the above method is applied to the return signals which correspond to a plurality of adjacent scan lines, which define a scan plane.

According to the reflected point nature discriminating analysis of the present method, the reflected points along a scan line determined to be contrast agents are those whose return signal has a fundamental component and a subharmonic component having similar or substantially identical amplitudes and a harmonic component having a lower amplitude than the fundamental and the harmonic components.

In fact, it was found that, by exciting the nonlinear reflected component with an appropriate acoustic pressure at the subharmonic of the fundamental transmission frequency, the intensity of said subharmonic component is substantially equal to that of the fundamental transmission frequency of the return signal.

In the method of the present invention, the second harmonic and subharmonic components are not used for ultrasonic imaging, but only to discriminate the areas of said image that correspond to regions of the body under examination which carry the contrast agent.

Regarding amplitude comparisons between the various frequency components of the return signal, the method of the invention provides a comparison of relative and not absolute amplitude values. In fact, there is no advantage in providing absolute amplitude thresholds for the harmonic, subharmonic and fundamental frequency components of the return signal, as the absolute amplitude value may vary depending on the type of tissue being examined. To this end, the invention provides an amplitude standardization for the above three components of the return signal, by using as a reference the amplitude value obtained for the fundamental transmission frequency component of the return signal. A simple relativization method consists in dividing the amplitudes of the three frequency components of the return signal by the amplitude of the return signal component at the fundamental transmission frequency, for each reflected point along each scan line.

As the propagation of the acoustic pulse in the body under examination is frequency-dependent, a proper reflector discriminating analysis, based on the amplitudes of the three frequency components of the return component, i.e. the fundamental, harmonic and subharmonic components, may be performed according to the invention based on an amplitude standardization step in which an amplitude compensation is provided for each return signal component at the fundamental, harmonic, and subharmonic transmission frequencies, which is a function of the transmitted signal penetration depth, the propagation time and the signal component frequency.

The inventive method may be practically implemented in several different modes. However, many ultrasonic probes have a narrow frequency band, typically of the order of 1.6 MHz to 3.2 MHz. Additional steps are often required to overcome these probe band width limitations.

A feasible, but cost ineffective and functionally inconvenient arrangement, consists in providing a specific probe for imaging processes with the above method. Apart from the additional cost of a special probe, each time this probe was needed the user would be required to connect the probe and reset the imaging apparatus to optimize its settings relative to the new probe.

Regarding the above mentioned narrow band of ultrasonic probes, the method implementation modes may be differentiated depending on specific applications relative to the body under examination. Particularly referring to diagnostic imaging, two specific fields of use are recognized. A first field of use is the radiological field, in which the regions of the body under examination include no moving tissues or organs, except blood or lymphatic flows.

Here, a simplified implementation mode may be provided. In fact, the time factor, i.e. the duration of the signal transmission and receive cycle is not critical, as organs are static and contrast agents remain therein for sufficiently long times.

Therefore, in the above conditions, the invention provides successive transmission of three identically focused ultrasonic beams, which are optimized for the fundamental frequency, the harmonic frequency and the subharmonic frequency respectively.

In combination therewith, a successive reception is also provided of three identically focused ultrasonic beams, which are optimized for the fundamental frequency, the harmonic frequency and the subharmonic frequency respectively.

More specifically, the method of the invention provides an array of transducers having a predetermined transmit/receive band width, where an upper band limit is defined which is twice the lower band limit. Three identically focused beams are successively generated, having a center frequency between the upper and the lower limits, a frequency corresponding to the lower limit of said band, and a frequency corresponding to the upper limit of said band. The return signal associated with the transmitted signal at the center frequency corresponds to the center or fundamental frequency component of the return signal. The return signal associated with the transmitted signal at the lower band frequency corresponds to the harmonic component of the return signal, and the return signal associated with the transmitted signal at the upper band limit corresponds to the subharmonic component of the return signal.

Hence, for each scan line, the fundamental, harmonic and subharmonic components of the return signal may be detected without replacing the probe.

In addition, the above arrangements also permit further optimization of the three identically focused transmitted beams relative to the return signal frequency component to be excited.

Indeed, the transmitted beam may be appropriately optimized for the fundamental component of the return signal in order to provide information for generating the B-mode background image. Here, the fired transmitted beam may be formed by at least one broad band, short duration pulse. This provides a better signal-to-noise ratio and an enhanced resolution.

However, for harmonic and subharmonic components, energy must be transferred to the reflectors. As reflectors are contrast agents, peak energy is not only unnecessary, but even harmful, for if acoustic pressure gets above a certain limit, there is the risk of breaking the microbubbles that form the contrast agents. Hence, in this case, the transmitted beam is optimized for the harmonic and/or subharmonic component of the return signal, to be a narrow band signal having a long duration. This obviously involves a decreased signal-to-noise ratio, a low resolution and the presence of artifacts. Nevertheless, as the method of the invention provides that such components only have reflector discriminating functions, such effects that might be considered inconvenient for imaging do not affect the result or the function of harmonic and subharmonic components of the signal. Also, transmitted beams having a predetermined acoustic pressure and a long duration are optimal for exciting harmonic and subharmonics.

By way of the above arrangements, the method of this invention yields a B-mode background image generated by the fundamental transmission frequency component of the return signal, i.e., the linear component of the return signal, that has a high quality and provides an enhanced resolution and an optimized signal-to-noise ratio. Reflector discrimination is performed by using transmitted beam firing parameters which ensure the best excitation effect on harmonic and subharmonic components, thereby providing an optimized detection of the presence of those components and an optimized amplitude measurement.

In addition to the use of a traditional transducer array, the method of the invention allows the transmission arrangements to be used for a particular transducer array, where the transducer array is divided into three different groups of transducers. The transducers of each of the three groups are excited to generate a transmitted beam at the center frequency between the upper and the lower band limits, a transmitted beam at the lower band limit frequency and a transmitted beam at the upper band limit frequency, respectively.

In accordance with the above arrangements, the transducer groups are excited in succession and are identically focused on the same scan line.

The above transmitting steps that provide a succession of three identically focused transmitted beams cannot be used when the imaging method is used for bodies under examination that contain moving tissues or organs, e.g. in cardiologic imaging applications. Here, the triplet of transmitted beams would be transmitted at different times, when the moving organ would exhibit different conditions. Therefore, the three different frequency components of the return signals would relate to a different moving organ condition for each frequency component of the return signal, thereby providing a less accurate evaluation.

In the case of moving organs within the body under examination, the invention provides an implementation mode that is different from the one that is described herein for radiological applications.

As a rule, in order to also implement the inventive method for imaging bodies containing moving organs or tissues or body parts, the invention provides the combination with a probe or a transducer array having a predetermined transmit/receive frequency band width range, wherein an upper band limit may be defined which is twice the lower band limit.

In order to overcome the potential inaccuracies experienced in using three successive transmission events as described above for use in radiological imaging, an embodiment of the invention permits the use of any type of method that introduces within the transmit beam duration the three different frequencies, i.e. the center frequency of the transducer array band between the lower and the upper limits and the frequencies of the lower and upper limits. In principle, several methods are known for detecting the frequency spectrum of the return signal to identify the transmission frequency, the harmonic frequency and the subharmonic frequency components of the return signal.

According to a first embodiment, the transmitted signal may be encoded to include the fundamental, harmonic and subharmonic frequencies, due to the fact that the transmitted beam is linearly modulated between the lower frequency limit and the upper frequency limit of the transducer band, within the duration of the transmitted beam, and where the received or return signal is accordingly demodulated to extract the return signal components at the fundamental frequency, corresponding to the center band frequency; the harmonic frequency, corresponding to the upper band limit; and the subharmonic frequency, corresponding to the lower band limit. This pulse modulation encoding, known as CHIRP, has been used for a long time in the radar field and may also find application in the electroacoustic field, due to the fact that the signals in use are still RF signals. A more detailed description of chirp modulation is contained in "Space-born Radar Remote Sensing: Applications and Techniques", Charles Elachi, Institute of Electrical and Electronics Engineers Press, New York, Dec. 1988. The document "Coded Excitation System for Improving the Penetration of Real-Time Phased Array Imaging Systems", Matthew O'Donnel, IEEE Transaction on Ultrasonics, Ferroelectrics and Frequency Control, Vol. 39, No. 3 May 1992, describes the application of a "Pseudo CHIRP" method in ultrasonic imaging, which document is integrated herein by reference.

According to a further alternative embodiment, the return signal is demodulated to extract the center band frequency, the upper band limit frequency and the lower band limit frequency components of the signal by using a time-frequency transform. A particular embodiment of the above method provides the use of a transform known as wavelet transform. A spectral map of the return signal may be generated to identify the center frequency between the upper limit and the lower limit of the band and the lower and upper limit frequencies of the band by sampling the return signal and processing the sampled and digitized signal by a discrete wavelet transform. The spectral map may then be analyzed, for example, by comparing it with reference spectral maps, which are used to identify the spectral map type and the reflector nature. This method is described in greater detail in U.S. Pat. No. 6,066,098, granted to the owner of this application, and whose content is integrated herein by reference.

The above are not the only arrangements that may be used in combination with the method of the invention. Other arrangements may be used for encoding the transmitted signals and for filtering the received signals by correlation, such as those described in U.S. Pat. No. 6,494,839, U.S. Pat. No. 5,961,463, U.S. Pat. No. 5,980,459 and U.S. Pat. No. 6,050,947, which are integrated herein by reference.

In most of the above mentioned ultrasonic pulse encoding methods, a considerable technical advantage is provided, in addition to the advantage of concentrating the excitation and detecting the fundamental, harmonic and subharmonic components within a single transmitted and received event, also has an advantage in that, while the pulse has a relatively long duration (and hence a low resolution), the encoding and correlated decoding of the pulse causes a signal compression during reception, which obviates the long duration of the signal and obtains images having quality similar to the that obtained by using broad band, short duration transmitted pulses.

This advantage is also combined with the fact that the peak acoustic pressure during transmission does not exceed the contrast agent destruction limits, yet due to signal compression obtained by the coding and decoding process, amplitude peaks are obtained, for at least some of the spectral components of the return signal, that have a sufficient amplitude for optimized imaging.

DESCRIPTION OF THE DRAWINGS

The characteristics of the inventive method and the advantages derived therefrom will appear more clearly from the following description of a few non limiting embodiments, illustrated in the annexed drawings, in which.

DETAILED DESCRIPTION OF THE EMBODIMENTS

The principle of the present invention consists in that ultrasound imaging of a body under examination is performed by exciting reflection echoes having components at the fundamental frequency of the exciting signal, at the subharmonic of said fundamental frequency and at the harmonic of said fundamental frequency. The reflector nature may be determined by analyzing the amplitudes of the ultrasonic imaging return signal for each reflected point, for instance along a scan line. There exists the need, in ultrasonic imaging, of differentiating whether the received return signal is due to the tissue or to a contrast agent that was appropriately used. While contrast agents are known to have a nonlinear reflection behavior, causing the presence of a return signal component at a harmonic frequency, e.g. the second harmonic of the fundamental frequency of the reflected signal, such nonlinear reflection behavior is also exhibited by biological tissues, particularly soft tissues. Hence, it is currently difficult to discriminate whether the nonlinear reflector that generates reflected signals having second harmonic components is a contrast agent or a nonlinear reflector, for instance, a soft biological tissue.

Such discrimination is of the utmost importance, as contrast agents are used to allow ultrasonic imaging of blood or lymphatic flows, which are known to be poorly echogenic and provide too little a contribution to the fundamental component, as compared with the same contribution generated by tissues. Therefore, it is important to positively identify the nature of the reflector that generated the harmonic component of the return signal.

To this end, it was found that if contrast agents were excited by appropriate acoustic pressures and by an appropriate energy transfer, they also generated, within the ultrasonic imaging return signal, subharmonic components of said signal, particularly at a first subharmonic of the fundamental transmission frequency.

On the other hand, such subharmonic component is almost absent or has very low amplitudes in return signals due to the reflection by either soft or hard biological tissues.

If contrast agents are appropriately excited, they generate return signal components at the first subharmonic of the fundamental frequency of the transmit signal, whose amplitudes are similar in all respects to those of the fundamental frequency component of the reflected signal.

Figure 1:
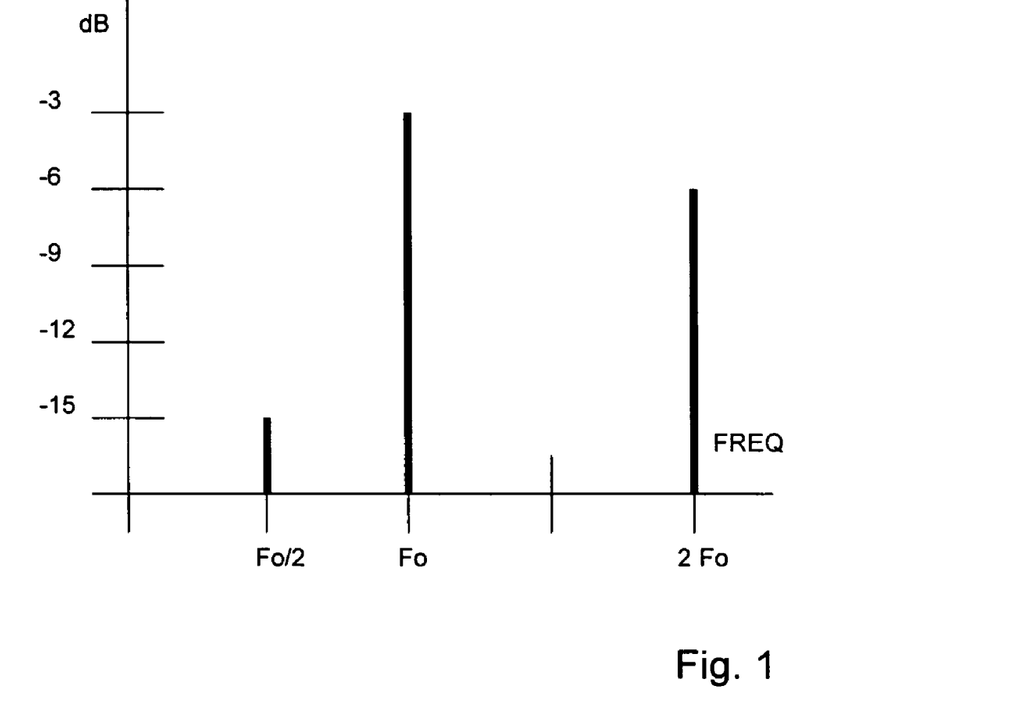
FIG. 1 shows the discretized spectrum of the return signal derived from a reflector consisting of a tissue of a body under examination, at the fundamental transmission frequency, at the second harmonic of the fundamental transmission frequency and at the first subharmonic of the fundamental frequency of the transmitted signal.
Figure 2:
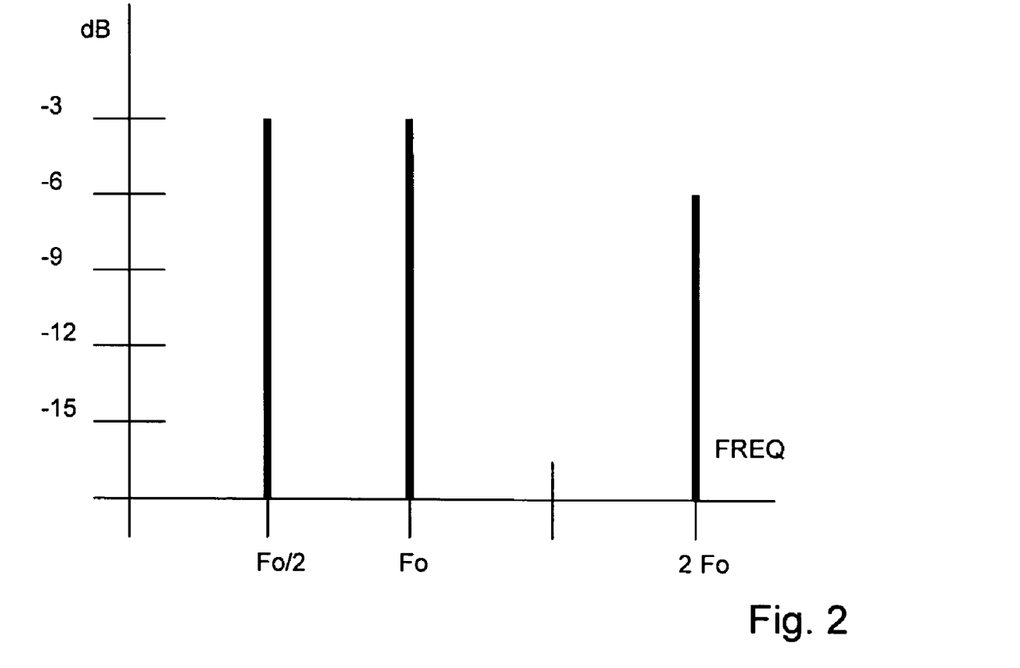
FIG. 2 is a diagram like that of FIG. 1, in which the spectrum relates to the return signal deriving from the contrast agent as a reflector.

FIG. 1 shows typical return signal components from biological tissues, at the first subharmonic of the fundamental transmission frequency, at the fundamental transmission frequency, and at the first harmonic of the fundamental transmission frequency. FIG. 2 shows typical return signal components from contrast agents at the three above mentioned frequencies. Such difference between the spectra of the two return signals somewhat constitutes a discriminant for determining the difference between reflector types, i.e. tissues and contrast agents.

The present invention provides a method wherein said three return signal components are determined and separated, and their respective amplitudes are stored to generate a diagram like that shown in FIGS. 1 and 2, in order to discriminate between tissue reflectors and contrast agent reflectors. Accordingly, an image is reconstructed by using the reflected signal component at the same frequency as the fundamental transmission frequency, as a B-mode image, for instance.

On the other hand, the discrimination between contrast agents and tissues permits the identification of B-mode image areas that correspond to the areas in which contrast agents were detected, in the manner described above. Subharmonic and harmonic components are not used to construct images, but only for the above mentioned reflector discrimination. The image areas corresponding to the reflectors that were identified as contrast agents are displayed on the B-mode grey scale generated by the fundamental component of the return signal by color variations or chrominance variations of the image areas.

As the B-mode background image obtained by the fundamental transmission frequency component of the return signal generally has an optimized resolution, and as contrast agents are only used to identify the presence of a flow, the method of the invention is particularly adapted to the purposes of the two imaging modes and yields a high quality background image and a highly reliable indication of the flow presence, as well as a highly reliable localization of said flows.

However, the implementation of the inventive method must account for the fact that ultrasonic probes have low-amplitude transmission and reception frequency bands. The frequency bands of probes are generally of about 1.6 MHz to 3.2 MHz. If a center frequency of 2.4 MHz is selected, both the subharmonic and the harmonic frequencies are outside the probe band. As a general rule, probes may be provided that have higher frequency bands, or multiple transducer arrays, each being optimized for such a frequency band that at least one of the arrays includes the subharmonic frequency and at least one of the arrays includes the second harmonic of the fundamental frequency. Hence, a first transducer array might include in its band a frequency of 2.4 MHz, whereas a second array is optimized for a frequency band including the first subharmonic frequency, i.e. 1.2 MHz, and a third array is optimized for receiving the first harmonic frequency, i.e. 4.8 MHz. This arrangement might obviate the above mentioned problems but is expensive and inconvenient for the user, who must replace or change the probe at each imaging process, with the added requirement that the probe will have to be calibrated for each probe change.

Figure 3:
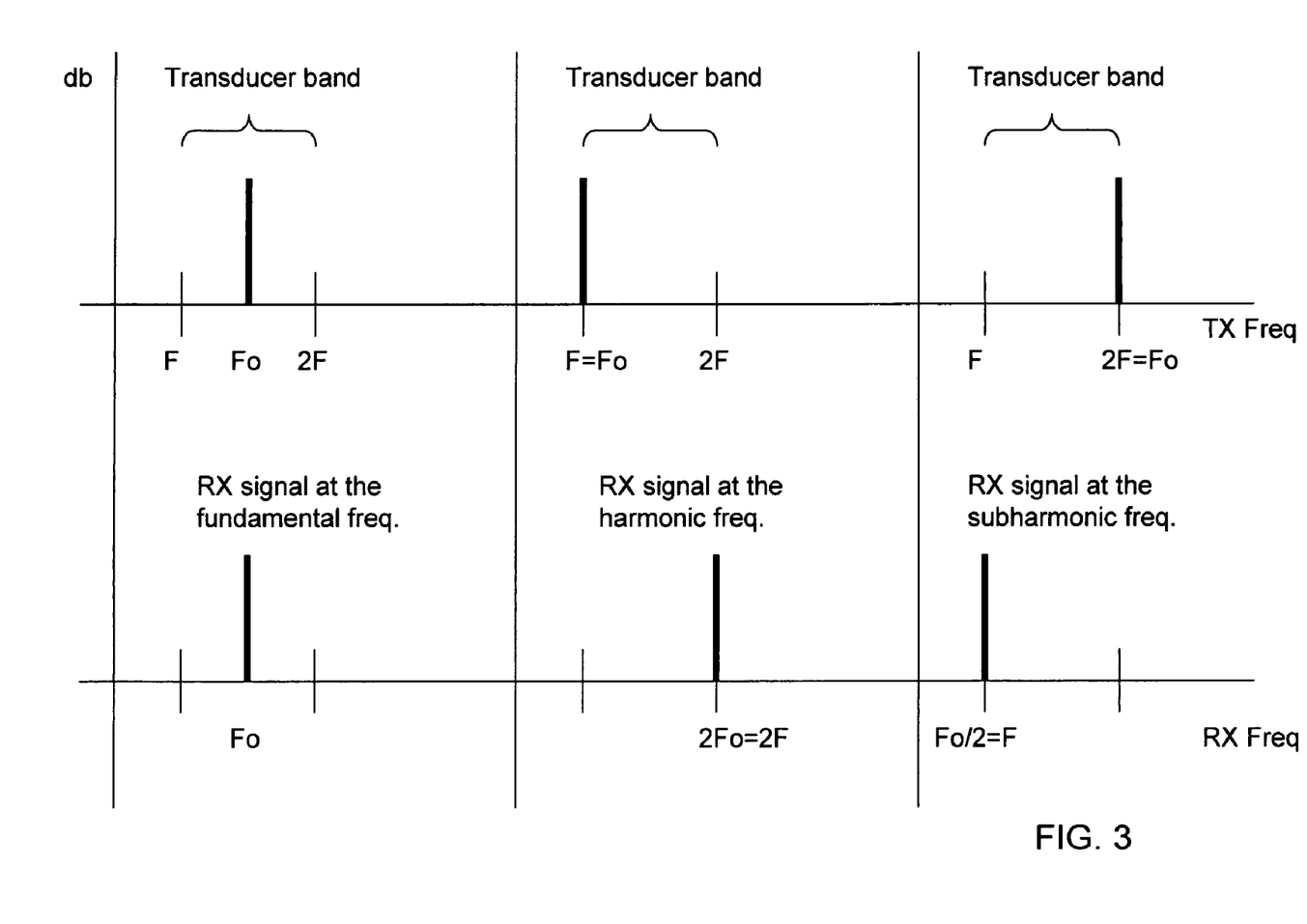
FIG. 3 is a diagram that shows the successive transmission of three identically focused beams at different fundamental transmission frequencies, such as to ensure that the return signal components corresponding to the fundamental transmission frequency, the subharmonic and the harmonic of each respective fundamental transmission frequency all fall within the frequency band of an array of transmitting and receiving electroacoustic transducers.

In radiological imaging, i.e., of bodies or regions of bodies containing stationary tissues and organs, such probe replacement problem might be obviated by generating a succession of three transmit beams for each scan line, each of which beams is optimized to transmit a fundamental frequency generating, within the frequency band of the probe, return signals having a fundamental frequency, a frequency equal to the first subharmonic of the fundamental transmission frequency and a frequency equal to the second harmonic of the fundamental transmission frequencies, which are all within the probe frequency response band. A simple way to obtain this is schematically shown in FIG. 3. When considering an ultrasonic imaging probe whose frequency band has a lower limit corresponding to half the upper limit, the three transmit beams are generated, the first being at the center frequency between the lower limit and the upper limit of the probe band. Here, the return signal component having the fundamental frequency of the transmit beam is separated and processed in the return signal. This is shown in the two superimposed diagrams at the left in FIG. 3. Referring to the previous example of a probe having a lower band limit of 1.6 MHz and an upper band limit of 3.2 MHz, the fundamental frequency of the transmitted beam and the frequency of the detected return signal component is of 2.4 MHz.

The second transmitted beam is transmitted at a frequency equal to the lower band limit and the return signal component whose frequency corresponds to the second harmonic of the fundamental transmission frequency is obtained from the return signal. This is shown in the central column of the diagram of FIG. 3. In the above example, the transmitted beam is transmitted at a frequency of 1.6 MHz, whereas the return signal includes the second harmonic component having a frequency of 3.2 MHz. In the right column of the diagram of FIG. 3, the third transmitted beam has a frequency corresponding to the upper band limit, whereas the component at the first subharmonic of said transmit signal is detected from the return signal. With reference to the above example, the fundamental transmission frequency is of 3.2 MHz, whereas the first subharmonic frequency is of 1.6 MHz.

The above described mode comprises a scan sequence whereby three transmitted beams having the above mentioned frequencies are successively transmitted. This method has the advantage of optimally adjusting the transmission parameters relative to the designed function of the corresponding return signal components. Hence, for example, the transmitted beam at the center frequency is optimized for detecting the return signal component at a center frequency that is designed for B-mode background imaging. In fact, in the method of the present invention, the transmitted beam at the center frequency of the band is a short, broad band, pulse. This permits an enhanced resolution and an optimized signal-to-noise ratio to be maintained, as well as reducing the presence of artifacts.

While the transmitted beams are optimized to receive the subharmonic and harmonic components of the transmission signal, there is no need for these components to provide a broad band pulse, as the subharmonic and harmonic components are not used for image reconstruction. Their presence is only needed to identify the nature of the signal reflectors, i.e. to recognize whether reflectors are tissues or contrast agents. For a proper excitation of harmonic and subharmonic components of the return signal, especially when contrast agents are present, the amplitude of the transmitted signal is not so critical as the amount of energy transferred to contrast agents, provided that acoustic pressure thresholds are not exceeded, in which case contrast agents would be broken. Therefore, the transmitted beams are optimized to receive harmonic and subharmonic components of the return signal formed by narrow band, long duration pulses, which are definitely inadequate to yield high quality images, but certainly more effective to excite nonlinear reflection responses from contrast agents.

Figure 5:
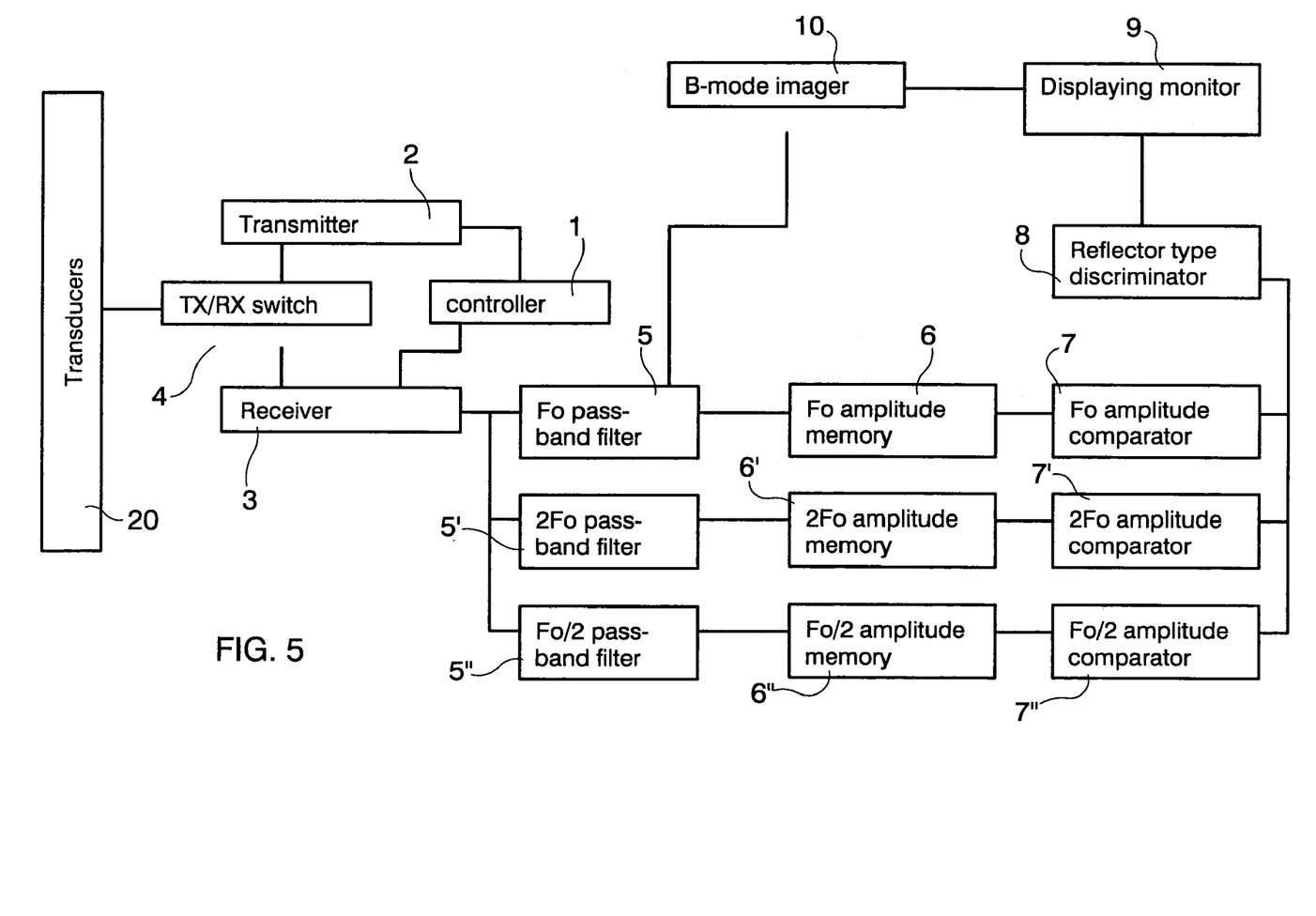
FIG. 5 schematically shows an ultrasonic imaging apparatus whereby the method of this invention may be implemented in a variant that provides successive firing of three identically focused transmit beams having different fundamental transmission frequencies, similar to that shown in FIG. 3.

FIG. 5 shows a chart of an ultrasonic imaging apparatus operating according to the above embodiment of the inventive method. Here, a central controller 1 controls the transmitter 2 and the receiver 3, which are in turn connected to the transducers 20 through a switch 4, the latter being synchronized with the transmit and receive steps. The signal that comes from the receiver 3 is bandpass filtered by filters 5, 5', 5" relative to the fundamental frequency of the transmitted beam, the second harmonic of the fundamental transmission frequency and the first subharmonic of the fundamental transmission frequency, respectively. The application of these filters is synchronized with the sequence of transmitted beams optimized for receiving the corresponding reflected signal component at the above frequencies. The return signal components for each reflected point along each scan line are stored in memories 6, 6', 6". Particularly, the amplitude of said components is stored. These values are standardized relative to the fundamental frequency amplitude and compared by comparators 7, 7', 7" with appropriate threshold values, particularly at least with regard to the subharmonic component of the return signal. The comparison result is routed to a discriminator 8, which generates signals for controlling a display monitor 9 for the pixels of said monitor that correspond to the image areas in which the signal received from the body under examination is due to contrast agents.

The fundamental components of return signals are processed by imager 10 for generating a B-mode image, to be displayed on the monitor 9. The discriminator controls the monitor pixel aspect in the areas of the B-mode image, i.e. the background image, corresponding to areas of the body under examination in which return signals have been identified that were assumed as being generated by contrast agents, according to the above method. The aspect of these pixels, corresponding to contrast agent signal contributions is controlled, for instance, by appropriate color assignment or chrominance variations. The image obtained thereby is a high quality image, in terms of resolution and sharpness, relative to the background B-mode image, and is highly reliable for the identification of contrast agents.

The above described method, which permits the obviation of the band width limits of prior art ultrasonic probes without using a special ultrasonic probe cannot unfortunately be used when the body under examination or the part thereof is a moving organ, tissue or part.

If this is the case, the return signal components at the transmission frequency, the harmonic frequency and the subharmonic frequency cannot be scanned by a succession of identically focused transmit beams, each optimized for one of said return signal components, as each of the three successive beams generates a return signal for a different condition of the subject being examined, because, in the time between two successive transmit beams, the subject being examined, for instance the organ, has moved; therefore the component of the return signal for a successive transmit beam cannot be compared with the preceding one.

In these conditions, the invention provides an alternative embodiment, wherein techniques are used for encoding and modulating the transmitted beam frequency, in order to modulate the transmission frequency within the duration of the transmit beam. As mentioned above, some of these techniques are known and currently used.

According to a first variant embodiment, the frequency of the transmitted beam is modulated linearly within the duration of the transmitted beam by varying the transmitted beam frequency from a start value to an end value, which form the limits of a predetermined band width. Referring to the probe that was mentioned above as an example, the frequency of the transmitted beam may be varied linearly within the duration of the transmitted beam from the frequency corresponding to the lower limit of the probe band to the frequency corresponding to the upper limit of the probe band. During reception, a demodulation of the frequency spectrum is required, which is correlated in time with the transmission modulation. This technique is known from RADAR technology as CHIRP.

Figure 4:
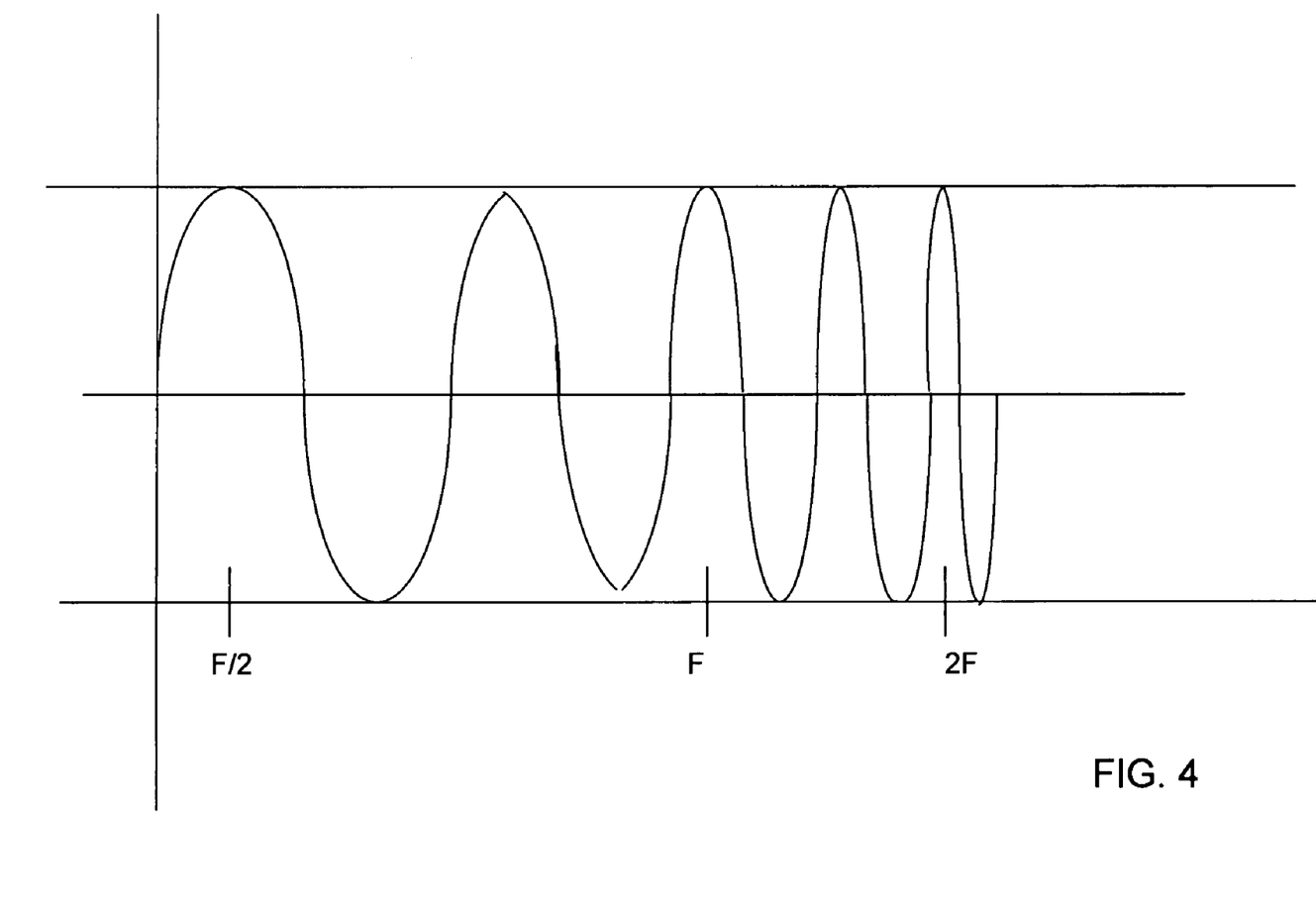
FIG. 4 shows an example of linear encoding of a transmit pulse frequency according to the CHIRP encoding method.

FIG. 4 shows the waveform of the transmitted signal for a linear chirp passing from a lower limit of the probe band equal to ½ Fo to an upper limit of the band equal to 2 Fo. Note that the wavelength decreases with time.

Other modulation types are provided which are not continuous and linear and involve phase and frequency hops in schemes of discrete steps. One of such techniques is known as Pseudo Chirp and is described in "Coded Excitation System for Improving the Penetration of Real-Time Phased Array Imaging Systems", Matthew O'Donnel, IEEE Transaction on Ultrasonics, Ferroelectrics and Frequency Control, Vol. 39, No. 3 May 1992. Demodulation or decoding is generally performed by correlated filtering of the return signal. Several other encoding and decoding techniques are described in U.S. Pat. No. 6,494,839, U.S. Pat. No. 5,961,463, U.S. Pat. No. 5,980,459 and U.S. Pat. No. 6,050,947 which are integrated herein as references.

Figure 6:
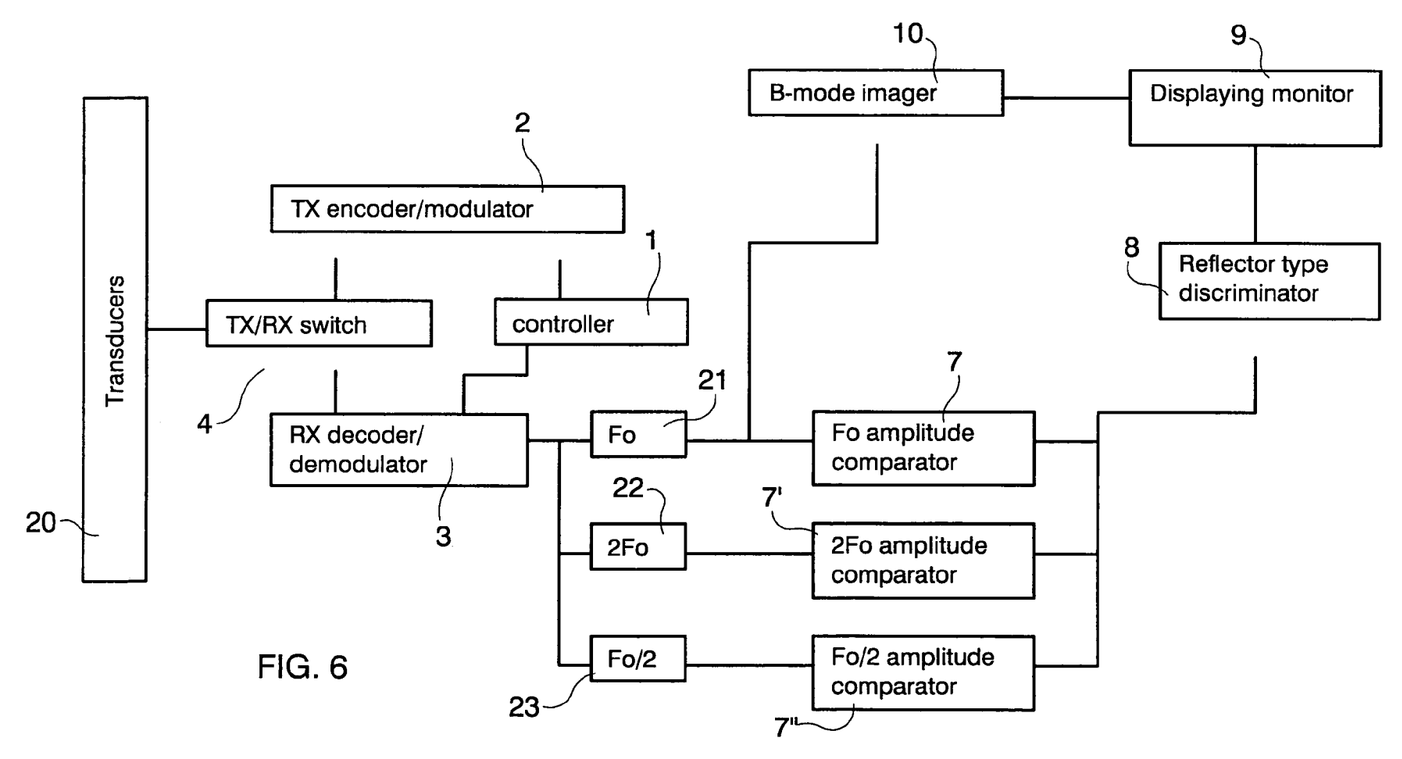
FIG. 6 schematically shows an ultrasonic imaging machine for implementing the inventive method in which the transmit beam is encoded or frequency modulated and the return signal is decoded/frequency demodulated while being correlated to the transmitted beam.

An apparatus for implementing the method of the invention using techniques for encoding/decoding or frequency modulation and demodulation for transmitted and received signal is schematically shown in FIG. 6. Here, parts that are equal to or have the same function as parts of the device as shown in FIG. 5 are denoted with the same reference numbers.

Transmission, encoding or modulation, and reception and decoding or demodulation are controlled by a controller 1. The transmitter 2 has encoder/modulator functions and the receiver 3 has decoder/demodulator functions. By encoding the transmitted signal to excite the return signal components at the fundamental transmission frequency, at the harmonic and at the subharmonic of the transmission frequency, it is possible to introduce in a single transmitted beam all the required optimizations to maintain the subharmonic and harmonic frequencies within the probe band.

Decoding or demodulation is often provided by correlations or convolutions and filtering. Particularly, a FIR filtering process is often used. The decoding or demodulation process yields the three separate components 21, 22 and 23 of the return signal for the single transmitted beam. These components are designated as Fo, 2 Fo and Fo/2, respectively, in FIG. 6. Now, the amplitudes of said components are detected and the processing thereof is substantially identical to the one discussed with reference to FIG. 5.

In addition to the above transmit signal encoding techniques, techniques may be also provided for detecting the spectral map of the return signal. In this case, the invention provides the use of a different technique, based on the Wavelet transform. The steps of this technique consist in generating a spectrum of the transmitted beam including the above mentioned three frequencies and in subsequently detecting, in a correlated manner, the spectral map of the return signal. The steps of this technique include sampling and digitization of the return signal, and subsequent processing by a Wavelet transform. The spectral map may then be analyzed, for example, by comparing it with reference spectral maps which are used to identify the spectral map type and the reflector nature. This method is described in greater detail in U.S. Pat. No. 6,066,098, granted to the owner hereof, and whose content is integrated herein by reference.

Figure 7:
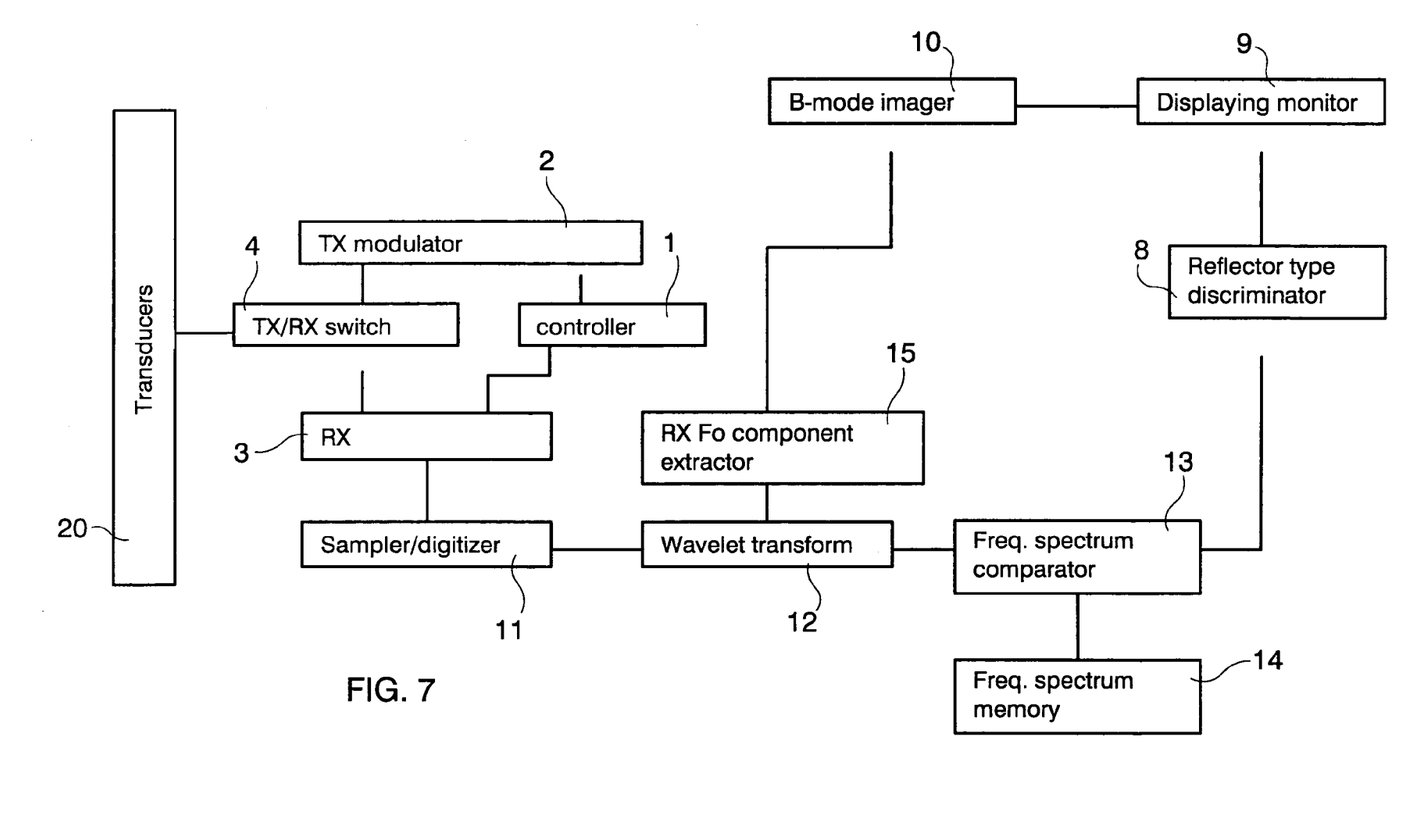
FIG. 7 schematically shows an ultrasonic imaging apparatus for implementing the method of this invention in which the frequency spectrum map of the return signal is determined and compared with typical reference spectra for the return signal due to the tissue and for the reflected signal due to contrast agents.

FIG. 7 shows a simplified scheme of an apparatus operating by detecting the spectral map of the return signal and comparing it with predetermined unique spectral maps to recognize the reflector nature-specific map. Unlike the previous embodiments, the signal coming from the RX receiver 3 is sampled and digitized by digitizer 11 and subjected to the Wavelet transform function 12. A spectral map is thus obtained for each reflector, and each map is then compared by comparator 13 with reference spectral maps stored in a memory 14 of the apparatus. Depending on the correspondence of the spectral map with one of the reference maps, the reflector is assigned a reflector type. Included in the FIG. 7 diagram is a component extractor 15.

Regarding the rest of the procedure of B-mode imaging and display from the return signal component at the transmission frequency, these steps are substantially identical or similar to those provided above for radiological use.

Obviously, the invention is not limited to the above description and figures, but may be greatly varied, and particularly the apparatus may be varied as regards construction, and the method may be varied by combination with other well-known imaging methods. All the above without departure from the inventive teaching disclosed above and claimed below.

What is claimed is:

1. An ultrasound method for use in the presence of contrast agent comprising the steps of:
   transmitting by an array of electroacoustic transducers at least one beam of acoustic waves into a body under examination, said body having a presence of contrast agents, said beam being transmitted at a first fundamental transmission frequency and being focused on at least one scan line;
   receiving said at least one beam reflected from said body under examination by using an array of receiving electroacoustic transducers, said transducers generating an electric return signal corresponding to said reflected beam along said at least one scan line;
   separating a subharmonic component from said return signal;
   storing said subharmonic component;
   after said storing step, determining the amplitude of said subharmonic component for at least one reflected point along said scan line; and
   comparing the amplitude of said subharmonic component to a predetermined minimum amplitude for determining whether said at least one reflected point is due to a contrast agent, wherein said stored subharmonic component is maintained.

2. The ultrasound method of claim 1, wherein said separating step includes separating a fundamental component and at least one harmonic component from said return signal; and
   wherein the determining step includes determining the amplitude of said fundamental component and said at least one harmonic component for said at least one reflected point along said scan line, and which further includes the step of comparing said amplitudes of the fundamental, harmonic and subharmonic components for at least one reflected point along said scan line.

3. The ultrasound method as claimed in claim 2, characterized in that it is applied to the return signals which correspond to a plurality of adjacent scan lines which define a scan plane.

4. The ultrasound method as claimed in claim 2, characterized in that said reflected points along said scan line determined to be contrast agents are those whose return signal has a fundamental component and a subharmonic component having similar or substantially identical amplitudes, and a harmonic component having a lower amplitude than the said fundamental and said subharmonic component.

5. The ultrasound method as claimed in claim 2, further including the following steps:
   generating a B-mode panoramic background image of said fundamental transmission frequency component of said return signal;
   providing a differential display, over a B-mode background image, by assigning one or more specific display colors and/or by chrominance variations, to the areas of said background images corresponding to said reflected points determined to be contrast agents.

6. The ultrasound method as claimed in claim 2, characterized in that the transmitted beam having a penetration depth and wherein for each return signal component, an amplitude compensation is provided which is a function of the transmitted beam penetration depth, a signal propagation time and a signal component frequency.

7. The ultrasound method as claimed in claim 2, characterized in that a successive transmission is provided of three identically focused ultrasonic beams, said beams being optimized for said fundamental frequency, said harmonic frequency and said subharmonic frequency, respectively.

8. The ultrasound method as claimed in claim 7, characterized in that a successive reception is provided of said three identically focused ultrasonic beams, said reception being optimized for said fundamental frequency, said harmonic frequency and said subharmonic frequency, respectively.

9. The ultrasound method as claimed in claim 2, characterized in that, in combination with an array of transducers having a predetermined transmit/receive band width, an upper band limit is defined which is twice a lower band limit, three identically focused beams are successively generated, a first one of said beams having a frequency between said upper and lower limits, a second one of said beams having a frequency corresponding to the lower limit of said band, and a third one of said beams having a frequency corresponding to the upper limit of said band, whereas the return signal associated with said first one of said beams is used for receiving the center or fundamental frequency component of the return signal, the return signal associated with said second one of said beams is used for receiving the harmonic component of the return signal, and the return signal associated with said third one of said beams is used for receiving the subharmonic component of the return signal.

10. The ultrasound method as claimed in claim 9, characterized in that said transmitted beam optimized for said fundamental component of the return signal is a broad band, short duration, high resolution beam.

11. The ultrasound method as claimed in claim 9, characterized in that said transmitted beam optimized for said harmonic and/or said subharmonic component of the return signal is a narrow band, long duration, low resolution beam.

12. The ultrasound method as claimed in claim 2, characterized in that said transducer array is divided into three different groups of transducers, said transducers of a first one of said groups are excited to generate a transmitted beam at the center frequency between the upper and the lower band limits, said transducers of a second one of said groups are excited to generate a transmit beam at the lower band limit frequency and said transducers of a third one of said groups are excited to generate a transmit beam at the upper band limit frequency.

13. The ultrasound method as claimed in claim 12, characterized in that said three groups of transducers are excited to generate three identically focused simultaneous transmitted beams.

14. The ultrasound method as claimed in claim 2, characterized in that in a transducer array having a predetermined transmit/receive frequency band width range, an upper band limit is defined which is twice the lower band limit, the frequency of the transmitted beam is linearly modulated between said lower band limit and said upper band limit within the duration of said transmitted beam, wherein said return signal is accordingly demodulated to extract said return signal components at a fundamental frequency, corresponding to a center band frequency, at said harmonic frequency corresponding to said upper band limit, and at said subharmonic frequency corresponding to said lower band limit.

15. The ultrasound method as claimed in claim 14, characterized in that said frequency modulation of said transmitted beam and the corresponding demodulation of said return signal are performed with a pulse modulation technique known as CHIRP.

16. The ultrasound method as claimed in claim 2, characterized in that in a transducer array having a predetermined transmit/receive frequency band width range, an upper band limit is defined which is twice the lower band limit, an ultrasonic transmitted beam is generated and frequency modulated to have a spectrum including signal components at a center frequency between said upper band limit and said lower band limit, signal components at said lower band limit and signal components at said upper band limit, wherein said return signal is demodulated to extract said signal components at said central frequency, at said upper band limit and at said lower band limit by using a time-frequency wavelet transform.

17. The ultrasound method as claimed in claim 16, characterized in that a spectral map of said return signal is generated to identify said center frequency between said upper band limit and said lower band limit, and said upper and lower band limits by sampling and digitizing said return signal and processing said sampled and digitized signal by a discrete wavelet transform.

18. The ultrasound method as claimed in claim 2, characterized in that in a transducer array having a predetermined transmit/receive frequency band width range, an upper band limit is defined which is twice a lower band limit, said transmitted beam being provided with a frequency spectrum comprising said lower band limit, a center frequency between said upper band limit and said lower band limit, and said upper band limit, said transmitted beam being modulated by encoding, with said fundamental, harmonic and subharmonic components of said return signal, corresponding to said center frequency, to said upper band limit and to said lower band limit, respectively, being extracted by correlated filtering.

19. The ultrasound method as claimed in claim 2, characterized in that the frequency spectrum of said transmitted beam is encoded by dividing said transducer array into at least two groups that are excited with predetermined phase differences and/or different frequencies.

20. The ultrasound method as claimed in claim 2, characterized in that amplitude comparisons between said components of said return signal are performed with reference to standardized amplitude values by using as a reference the amplitude value obtained for said fundamental frequency component of said return signal.

21. The ultrasound method as claimed in claim 20, characterized in that said standardization includes the determination of the quotient determined by each of said amplitudes of said return signal components at said fundamental transmission frequency, at said harmonic and at said subharmonic frequencies compared to said amplitude of said return signal component at said fundamental transmission frequency, for each reflected point along each scan line.

* * * * *